United States Patent [19]
Bell et al.

[11] Patent Number: 5,445,152
[45] Date of Patent: Aug. 29, 1995

[54] KINEMATIC DEVICE FOR PRODUCING PRECISE INCREMENTAL FLEXING OF THE KNEE

[75] Inventors: Rodney E. Bell, Kalamazoo, Mich.; Marc S. Kreidler, Sunnyvale; David T. H. Hung, Palo Alto, both of Calif.; Robert L. Moya, Edmonds, Wash.; Harrie J. M. Wolters, Menlo Park, Calif.

[73] Assignee: Resonex Holding Company, Fremont, Calif.

[21] Appl. No.: 979,532

[22] Filed: Nov. 23, 1992

[51] Int. Cl.⁶ ............................................. A61B 5/055
[52] U.S. Cl. .................................. 128/653.5; 5/601; 5/624
[58] Field of Search ............... 128/653.2, 653.5, 774, 128/779, 782; 601/34, 35; 5/601, 621, 624, 648, 650

[56] References Cited

U.S. PATENT DOCUMENTS

| 4,823,807 | 4/1989 | Russell et al. | 128/782 |
| 4,834,112 | 5/1989 | Machek et al. | 128/777 |
| 5,122,106 | 6/1992 | Atwood et al. | 601/34 |
| 5,154,178 | 10/1992 | Shah | 128/653.5 |

FOREIGN PATENT DOCUMENTS

| 4322639 | 11/1992 | Japan | 128/653.5 |

OTHER PUBLICATIONS

Radiology, Sep. 1989, vol. 172, No. 3 pp. 799–804. article entitled "Patellar Tracking Abnormalities: Clinical Experience with Kinematic MR Imaging in 130 patients".

Advertising Brochure, "A Positioning Device for Static and Kinematic MRI of the Knee" (Peter Sullenberger).

*Primary Examiner*—Ruth S. Smith
*Attorney, Agent, or Firm*—Flehr, Hohbach, Test, Albritton & Herbert

[57] ABSTRACT

A kinematic device for producing precise incremental movement in the knee of a human patient for the purposes of producing a cinematic type display of MRI images with the knee at different angles of articulation includes a platform on which the patient lies on his side within the imaging volume of an RI apparatus. The one leg/knee being examined is restrained on a sagittal plane parallel to the horizontal platform and the other leg is elevated to allow movement of the calf of the leg being examined to move thereunder for full articulation. Examination of the other knee is provided by allowing for reversibility of a leg rest and other essential components. Also a remote drive is provided for the angle of articulation as well as a digital readout of such articulation.

6 Claims, 7 Drawing Sheets

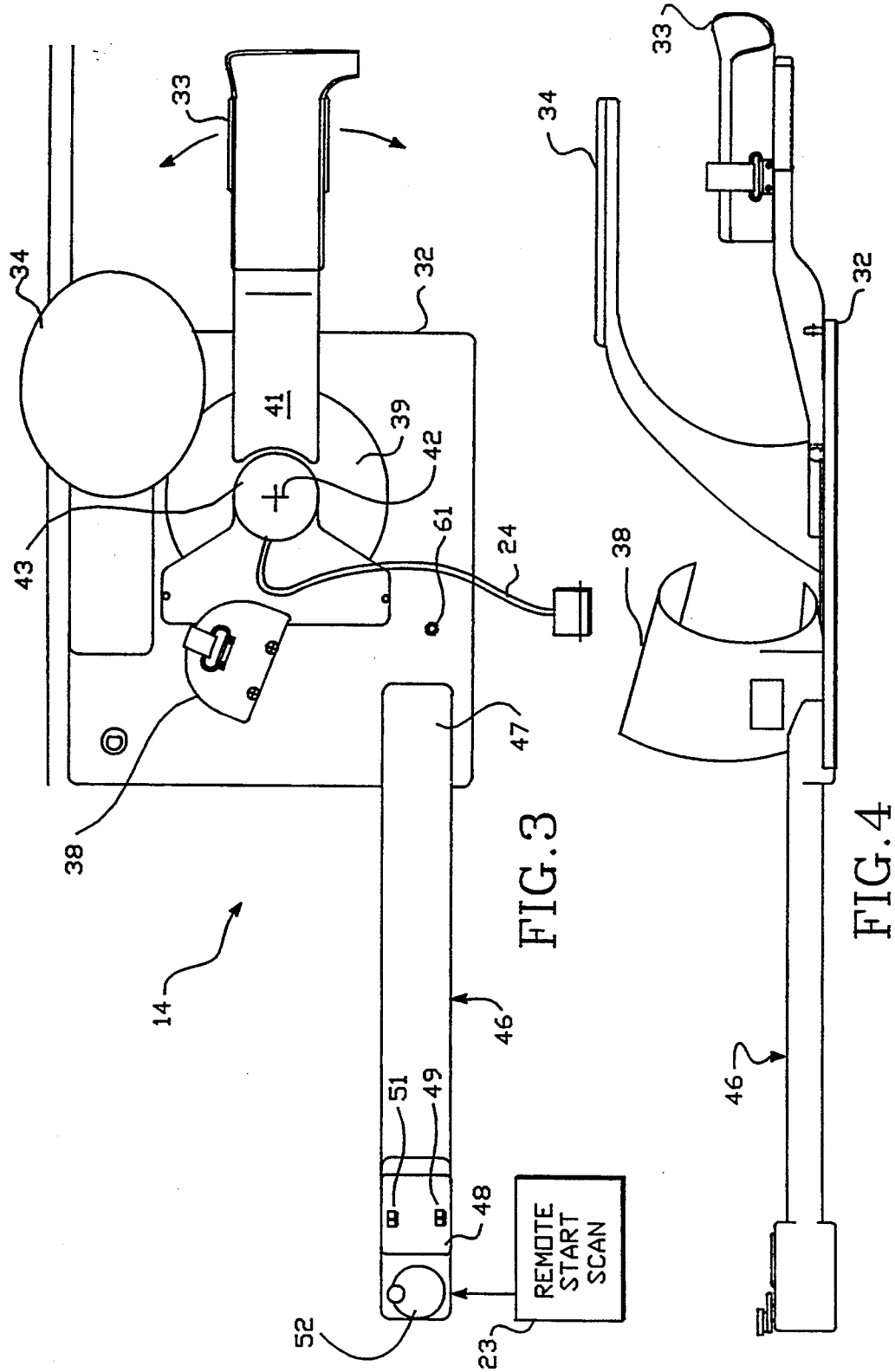

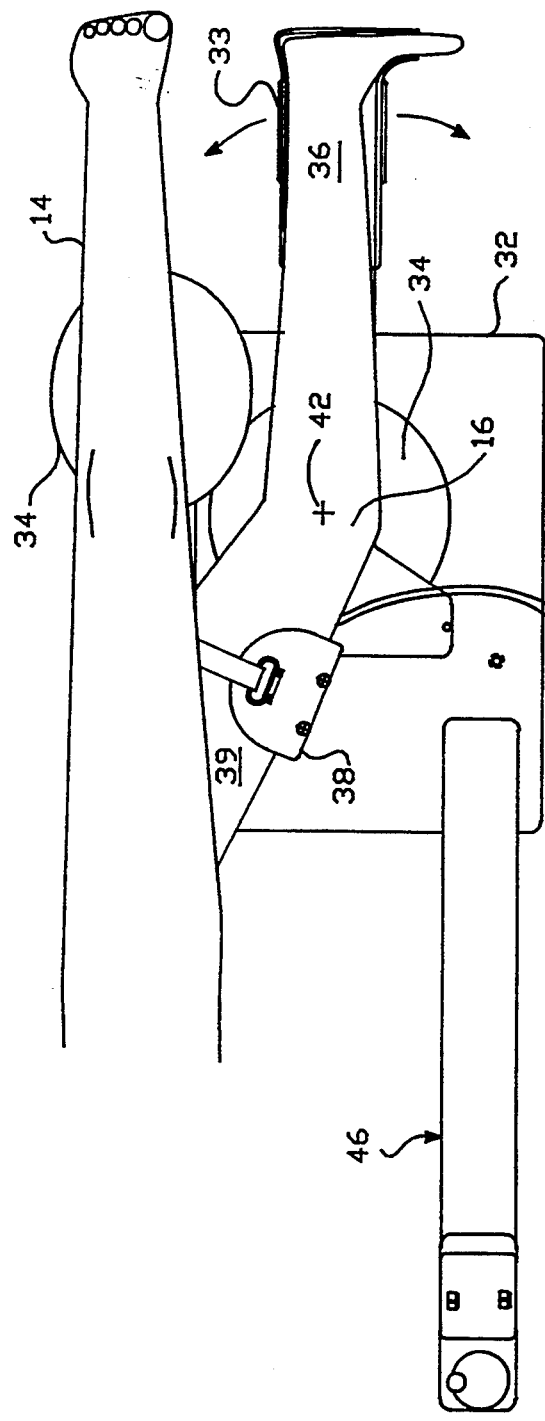
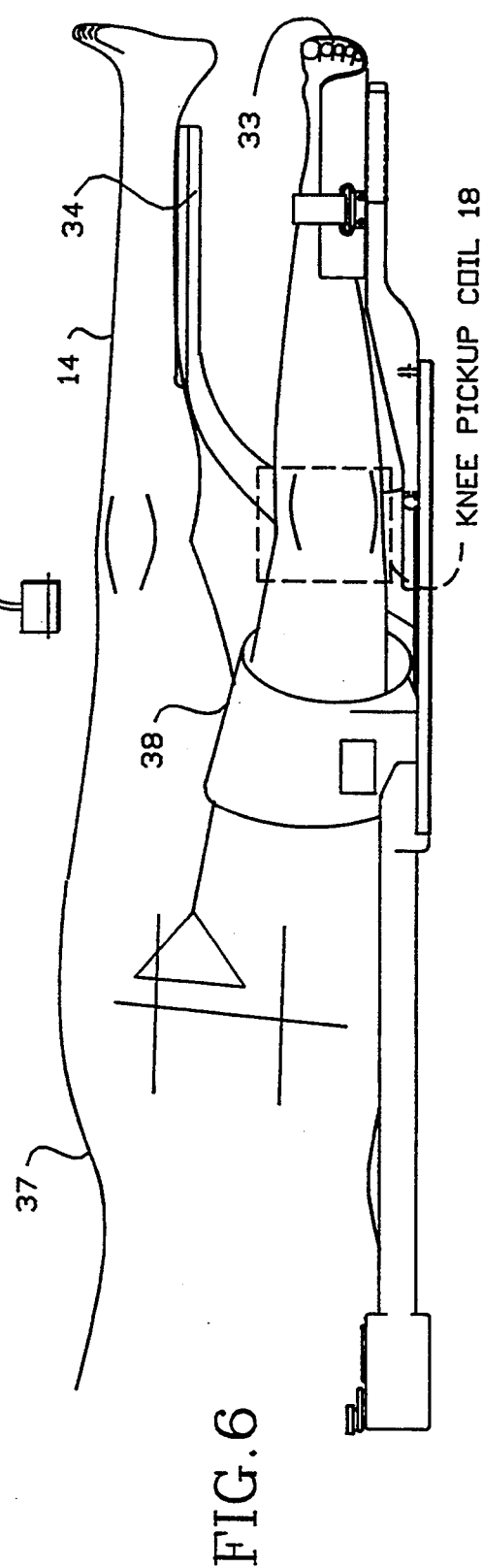
FIG.5
FIG.6

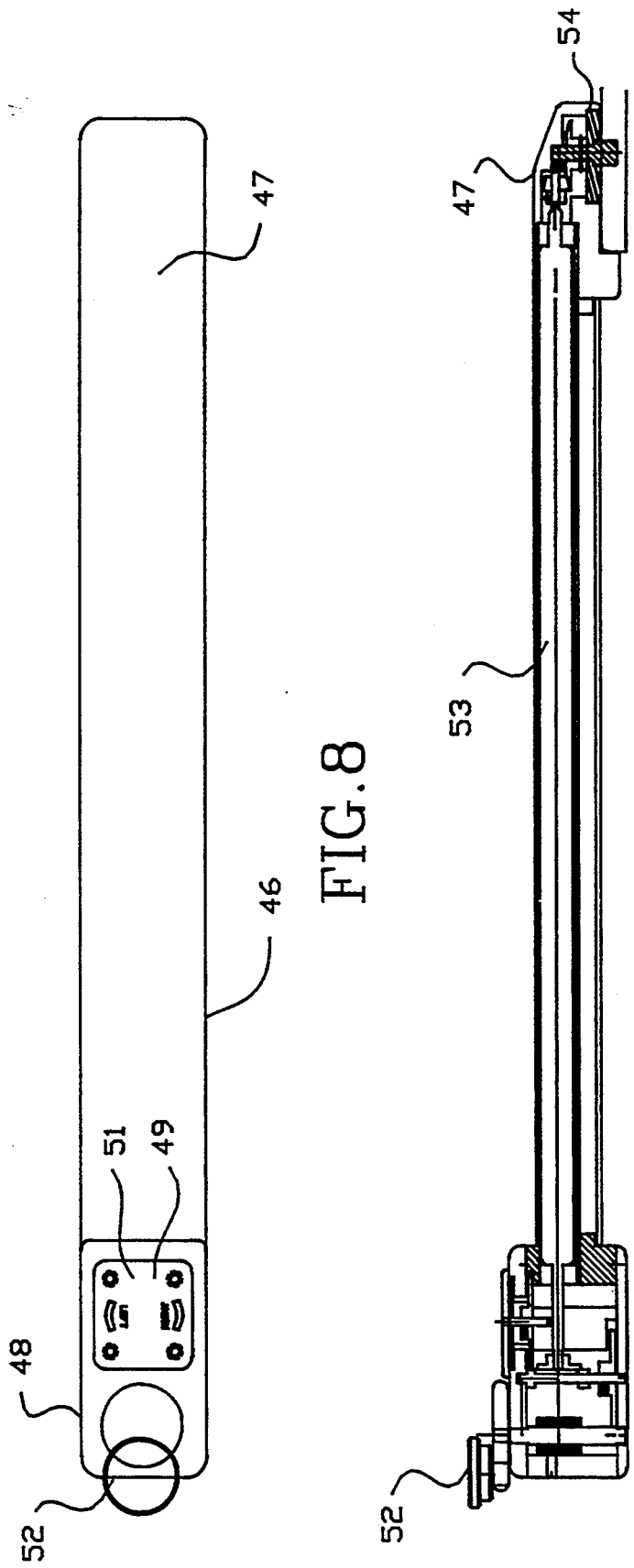

KINEMATIC DEVICE FOR PRODUCING PRECISE INCREMENTAL FLEXING OF THE KNEE

The present invention is directed to a kinematic device for producing precise incremental movement in the knee and, more specifically, where the knee is being examined in a magnetic resonance imaging (MRI) apparatus, and where a cinematic video tape is produced.

BACKGROUND OF THE INVENTION

Kinematic MRI imaging of the knee has been done before, both by manual manipulation of the knee or with some type of positioning device. During the MRI examination which may take some extensive period of time due to the necessity of acquiring several "slices" of the knee, the patient when inside of the aperture of the MRI apparatus must be made as comfortable as possible. At the same time it is desirable that the positioning device allow for easy flexing of the knee or its articulation from both an operator's standpoint for convenience, the patient's standpoint as far as comfort, and to obtain high quality MRI images.

A prior positioning device utilized a prone (face down) position of the patient which was not believed to offer adequate comfort. Also since space in the aperture of the MRI apparatus either with the main magnetic field in the vertical or horizontal direction is very limited, it must be taken into consideration in positioning the patient and at the same time provide for adequate articulation or movement of the knee.

OBJECT AND SUMMARY OF THE INVENTION

It is therefore a general object of the present invention to provide an improved kinematic device for producing precise incremental movement in the knee of a human patient.

In accordance with the above object, there is provided a kinematic device for producing precise incremental movement in the knee of a human patient while avoiding movement of the knee in its sagittal plane and any movement of the associated thigh comprising a platform movable into the aperture of a magnetic resonance imaging (MRI) apparatus for carrying at least the knee of one leg of said patient into an imaging volume of the MRI apparatus. Means are mounted on the platform for elevating the other leg of the patient to allow movement of the calf of the one leg under the elevated leg in the sagittal plane and to allow positioning of the patient substantially on his side whereby full flexure of said knee is allowed. The thigh is clamped to a fixed location on the platform. Means are mounted for rotation on the platform in said sagittal plane at substantially the flexure point of the knee. The calf is clamped to and for rotation with the means for rotation. Means are provided for incrementally isolating the means for rotation whereby the knee is incrementally flexed.

BRIEF DESCRIPTION OF DRAWINGS

FIG. 3 is a top view of platform and positioning apparatus embodying the present invention.

FIG. 4 is a side view of FIG. 3.

FIG. 5 is a top view similar to FIG. 3 but showing a human patient in the apparatus.

FIG. 6 is a side view of FIG. 5.

FIG. 8 is an enlarged top view of another portion of the apparatus shown in FIG. 3.

FIG. 9 is a side view of FIG. 8.

DETAILED DESCRIPTION TO PREFERRED EMBODIMENT

Figure 1:
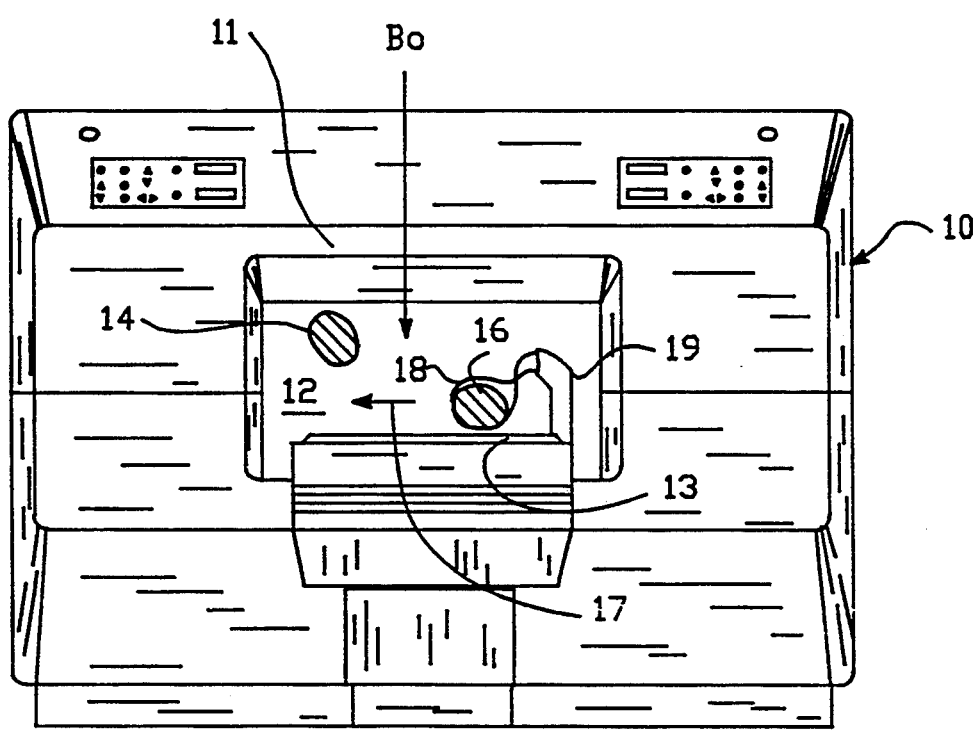
FIG. 1 is a perspective view and mainly a side elevation of MRI apparatus also showing the cross-section of the legs of a human patient contained within the aperture.

FIG. 1 is an end view of MRI apparatus 10 which, of course, includes a magnet with a magnetic field $B_0$ in a vertical direction. The patient to be examined is placed through the aperture 11 into the imaging volume 12. The patient is placed on a slidable sled-like platform 13 with a part of the body in the imaging volume 12. As is quite apparent, space is limited since the aperture size might typically be 37.5 by 81.3 centimeters. In accordance with the present invention which is useful for taking several slice type images of the human knee, there is illustrated cross-sections of 14 and 16 of the knee portions of the left and right legs of the patient who would be substantially lying on his side. That is, knee 16 or the sagittal plane through it would be parallel to the horizontal platform 13. Thus as indicated by the arrow 17 a kinematic positioning device by elevating the leg 14 allows the calf of the knee 16 to be fully flexed in the direction shown by the arrow 17 to pass under the leg 14.

Finally to provide the actual MRI image there is shown a belt type coil 18 wrapped around the knee 16 which is supported by the belt coil tower 19. Such belt and coil tower are disclosed and claimed in U.S. Pat. No. 4,791,372, assigned to the present assignee. In addition the sled like platform is also disclosed and claimed in U.S. Pat. No. 4,771,785. Finally the magnetic structure of the MRI apparatus with a rectangular aperture is disclosed in U.S. Pat. No. 4,791,370.

Figure 2:
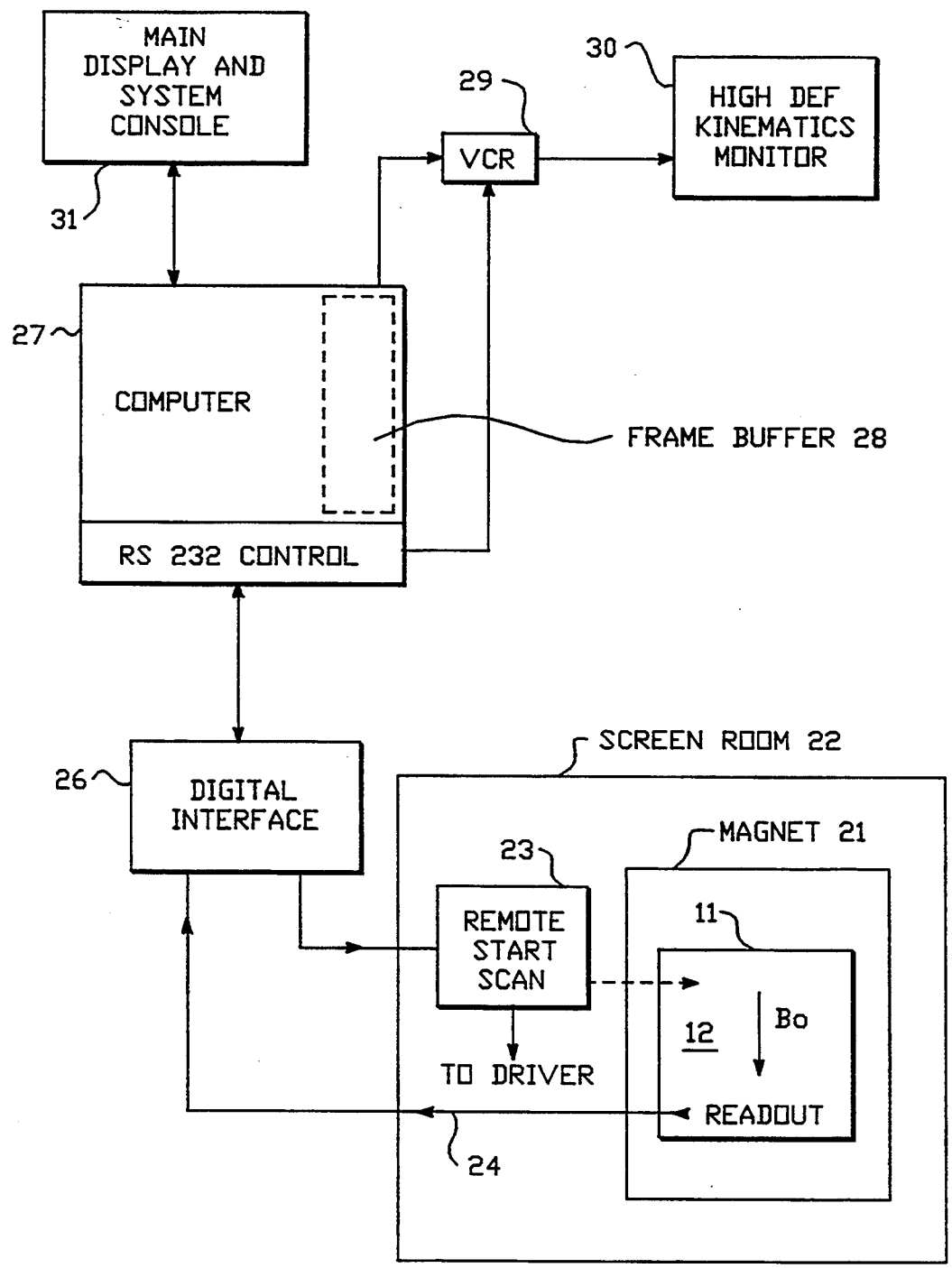
FIG. 2 is a block diagram of the present invention.

FIG. 2 illustrates the MRI apparatus 10 of FIG. 1 showing its magnet 21 to produce the magnetic field $B_o$ with the aperture 11 and the imaging volume 12. The entire MRI apparatus is, of course, contained within a screen room 22 to prevent interference from external electromagnetic signals and noise. In general, the apparatus of FIG. 2 provides for a kinematic positioning device for the knee/leg 16 illustrated in FIG. 1 which within the volume 12 flexes the knee to provide a series of MRI images. These then may be combined to be shown as a combination of joint angles in a fast sequence display giving the effect of kinematic motion. To accomplish this within the screen room 22 there is a remote start scan device 23 where the MRI system operator can assist the patient with joint movement during the kinematic acquisition. This is coupled, as indicated, to a "driver" which will be illustrated in detail below. Then the angle of joint articulation is read out by an encoder system on line 24 and coupled to a digital interface unit 26 along with the control line to remote scanning unit 23. This is coupled to an RS 232 control unit which is part of computer 27. In addition the computer 27 includes a printed circuit frame buffer 28 (for example, Imaging Technology Model FG-100) with a capacity of 1 megabyte of video memory thus allowing 256×256 images to be loaded. Once the images have been stored in video memory, the frame buffer has the ability to cycle between images very quickly simulating real-time motion. The frame buffer 28 is coupled with the VCR unit 29 and then to a high definition kinematics monitor 30. Finally the computer 27 includes a standard main display/system console 31.

FIG. 3 (along with a side view of FIG. 4) indicates a kinematic positioning device which may be an integral part of platform 13 or more typically placed on that platform. The kinematic positioning device includes an essentially square base 32 which is placed on the platform 13. A leg rest 34 best shown for its leg elevation aspect in FIG. 4 is fixed to the base 32 and serves to elevate the other leg of the patient (the one which is not being imaged) to allow the leg being imaged to move below it. Specifically the one leg being imaged is fixed to a calf/foot restraint 33. This is more succinctly shown in FIGS. 5 and 6 also. The elevation provided by the leg rest 34 allows the movement of the calf of one leg, specifically 36 in FIG. 5, under the elevated leg 14 to provide for full flexure of the leg/knee 16, which as discussed above has its sagittal plane through the knee essentially parallel to the horizontal base 32 and the supporting platform 13. This allows the patient, as illustrated in FIGS. 5 and 6, to be substantially positioned on his side. Such side positioning is essential in providing greater range of motion of the knee (as well as the lower spine joints if these are being examined). At the same time, it ideally positions the entire body 37 (see FIG. 6) in the relatively constricted aperture 11 (see FIG. 1).

To provide for a repeatable series of images of the articulated knee in different flex positions, it necessarily must take place at different moments of time because of the several second time requirement for each MRI image. There is provided affixed to base 32 a thigh cuff or restraint 38. This clamps the thigh 39 of the right leg of the patient, as best illustrated in FIGS. 5 and 6. Thus the thigh while the knee is being flexed is maintained relatively immovable to thus provide an effective series of repeatable images.

To flex the knee, the foot/calf restraint is mounted on a rotatable disk 39 by an extension 41 of the calf/foot restraint 33 which is fixed to the rotatable disk 39. This has a center of rotation at 42 which as illustrated in FIG. 5 is essentially the flexure point of the knee. Thus the calf/foot restraint 33 flexes the knee by rotating it in the sagittal plane which of course is the longitudinal plane going through the knee.

Movement of disk 39 and its associated calf/foot restraint 33 is sensed by an angular encoder 43 mounted of course at the center of rotation 42. Although not shown in detail, it is of relatively standard construction using a reflective code disk with a light emitting diode and a photocathode sensing a rotation by rotation of the reflective spokes of the disk. In general, it has an angle range from a −10° to a possible 246°. This digital readout appears on line 24 (see FIG. 2) and is processed by digital interface 26 and computer 27. Then the articulation or flexure of the kneel is displayed on both display 31 and the kinematics monitor 30.

Figure 7:
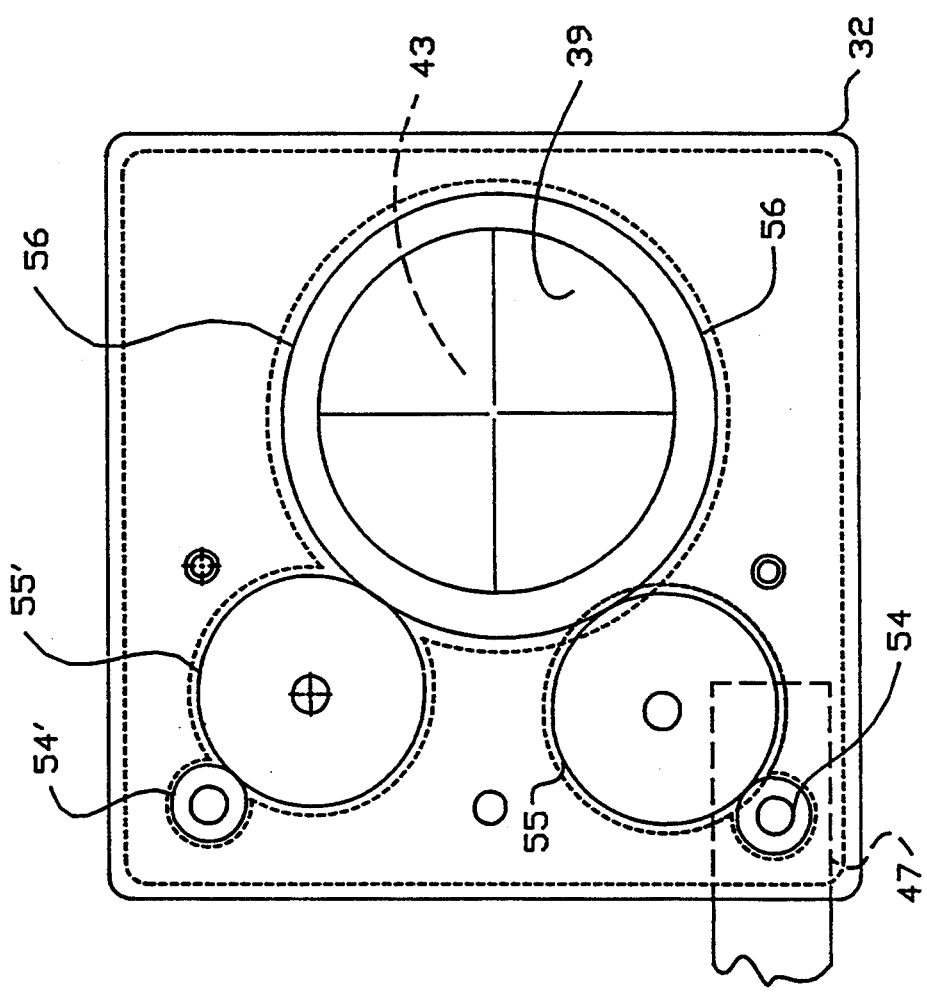
FIG. 7 is a top view in greater detail of a portion of the apparatus shown in FIG. 3.

To incrementally rotate foot restraint 33 on the disk 39 there is provided a driver unit 46 (see FIG. 3) which is an elongated device having one end 47 affixed to base 32 to mesh with a gear contained in the base as will be described below, and the other end 48 having visual angle displays 49 and 51 for the right and left legs and a manual drive unit 52. In addition there is a remotely operable drive unit (remote start scan 23 discussed in conjunction with FIG. 1) which may be started by the operator to provide a predetermined incremental motion or be controlled by computer activation. In any case the foregoing is clearly outside of the aperture to allow easy operation. Incremental drive unit 46 is better illustrated in FIGS. 8 and 9 where the manual rotation knob 52 is geared to an elongated drive shaft 53 which then drives a spur gear 54 at the end 47. The coupling of the end 47 of the drive system to the rotatable disk 39 of platform base 32 is best shown in FIG. 7. End 47 with its spur gear 54 meshes with an idler gear 55 which in turn meshes with another driven spur gear 56 which is actually a portion of or rotates with the rotatable disk 39. Then for reversibility of the system where if a left knee rather than a right knee is to be imaged, as illustrated, there is provided a spur gear 54' which would be inserted in that location along with an idler 55 which again drives the spur gear 56.

Figure 10:
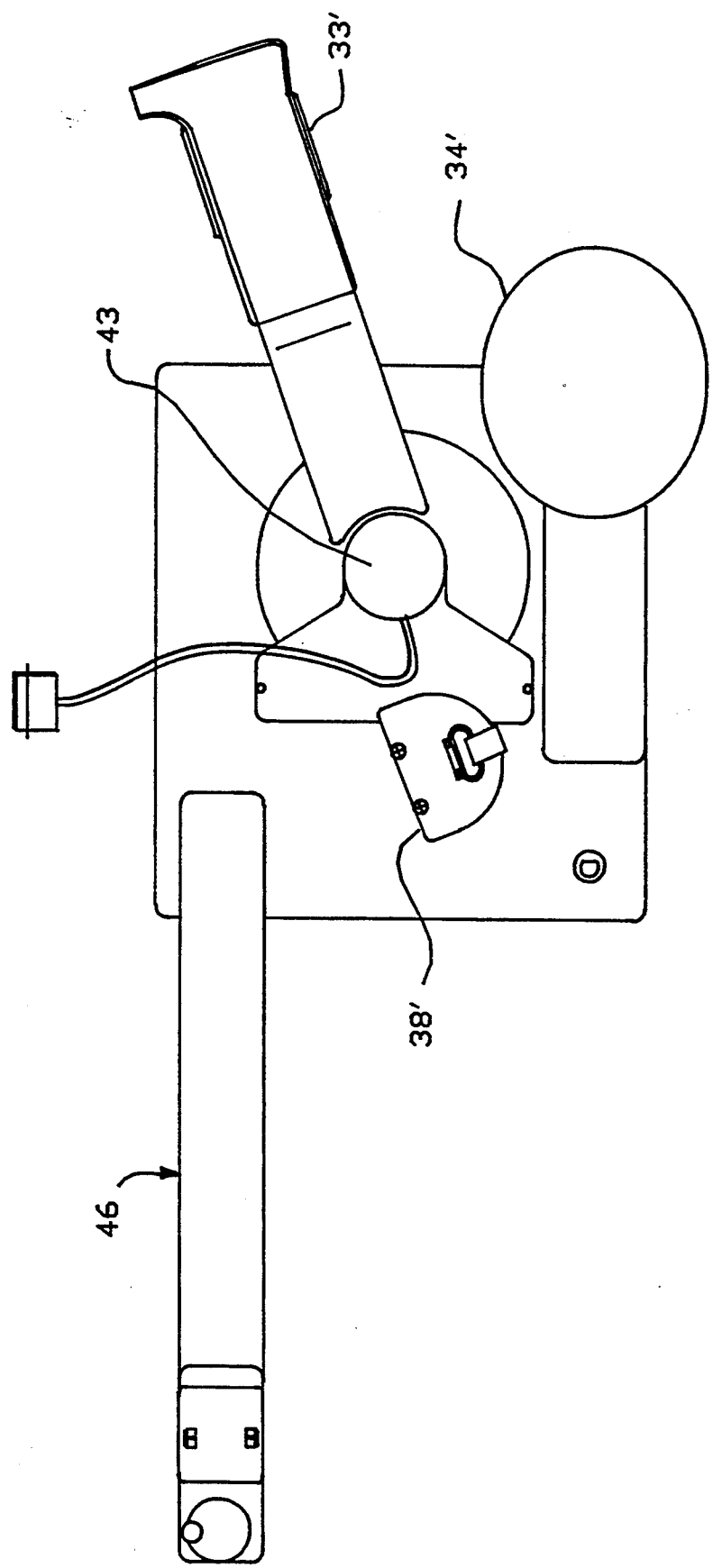
FIG. 10 is a top view similar to FIG. 3 but illustrating the use of an opposite leg.

And referring to reversibility, FIG. 10 illustrates the kinematics positioning device for a study of the left knee where the driver arm 46 would be installed in an opposite location on the other side of the platform as compared to that illustrated in both FIGS. 3 and FIG. 7. The calf/foot restraint unit 33 is reversed 180° from that shown in FIG. 3, and of course, the leg rest 34' is reversed. And the fastener 61 for the leg rest is illustrated in FIG. 3 for the other position of the leg rest.

Finally the thigh restraint 38 as illustrated in FIG. 10 is now 38' and it is located in a reverse position to accommodate the thigh. It is also angularly moved to provide a convenient initial starting position for the calf/foot restraint 33'.

Thus, in summary, to provide for left and right imaging leg rest elevating means, the driver and the leg restraint are alternately mounted at or near opposite longitudinal edges of the platform 13.

Thus an improved kinematics device for producing precise incremental movement of the knee of a human patient has been provided.

What is claimed is:

1. A kinematic device, for use with magnetic resonance imaging (MRI) apparatus having an aperture, for producing precise incremental flexing movement of the knee of a human patient while substantially avoiding movement of the flexure point of the knee in its sagittal plane, movement of said knee perpendicular to said plane and any movement of the associated thigh comprising:

a horizontal platform movable into said aperture for carrying at least the knee of one leg of said patient into an imaging volume in said aperture, said one leg also having a thigh;

means mounted on said platform for elevating the other leg of said patient to allow movement of the calf of said one leg under said elevated leg in said sagittal plane and to allow positioning of the patient substantially on his side whereby full flexure of said knee is allowed;

means for clamping said thigh to a fixed location on said platform;

means mounted for rotation on said platform in a horizontal plane and having a center of rotation;

means for clamping said calf to and for rotation with said means for rotation and for locating said flexure point of said knee at said center of rotation;

means for incrementally rotating said means for rotation whereby said knee is incrementally flexed.

2. A kinematic device for producing precise incremental flexing movement of the knee of a human patient as in claim 1 where said means for rotation includes a spur gear driven by said means for incrementally rotating.

3. A kinematic device for producing precise incremental flexing movement of the knee of a human patient as in claim 2 where said means for incrementally rotating includes drive extension means adapted to extend to the outside of said aperture to allow actuation manually or automatically and where said platform includes a pair of idler gear means mounted near opposite longitudinal edges of said platform and meshing with said spur gear for allowing said drive extension means to be alternatively positioned near either of each edges.

4. A kinematic device for producing precise incremental flexing movement of the knee of a human patient as in claim 1 where said means for incrementally rotating includes drive extension means adapted to extend the outside of said aperture to allow actuation manually or automatically.

5. A kinematic device for producing precise incremental flexing movement of the knee of a human patient as in claim 1 including belt coil RF pickup means for wrapping around said knee for providing MRI images of a plurality of different flex positions of said knee.

6. A kinematic device for producing precise incremental flexing movement of the knee of a human patient as in claim 1 including means for alternatively mounting said elevating means near either opposite longitudinal edge of said platform, to provide for elevation of the left or right leg of said patient.

* * * * *